(12) United States Patent
Yamada et al.

(10) Patent No.: US 7,832,594 B2
(45) Date of Patent: Nov. 16, 2010

(54) LIQUID STORAGE CONTAINER WITH BOTTOM FILTER

(75) Inventors: Hiroshi Yamada, Osaka (JP); Naohito Miyoshi, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 625 days.

(21) Appl. No.: 10/584,656

(22) PCT Filed: Dec. 24, 2004

(86) PCT No.: PCT/JP2004/019307

§ 371 (c)(1), (2), (4) Date: Jun. 26, 2006

(87) PCT Pub. No.: WO2005/063165

PCT Pub. Date: Jul. 14, 2005

(65) Prior Publication Data

US 2007/0145076 A1    Jun. 28, 2007

(30) Foreign Application Priority Data

Dec. 26, 2003    (JP) ............... 2003-434140

(51) Int. Cl.
  *B67D 7/76* (2010.01)
  *B65D 47/18* (2006.01)

(52) U.S. Cl. .......... 222/189.06; 222/420; 222/422; 222/83; 222/89; 222/91; 222/212; 604/295

(58) Field of Classification Search ............ 222/189.09, 222/420–422, 212, 213, 81–83.5, 87–89, 222/91, 189.06, 206; 604/295, 298

See application file for complete search history.

(56) References Cited

U.S. PATENT DOCUMENTS

| | | | | |
|---|---|---|---|---|
| 4,002,168 A | | 1/1977 | Petterson | |
| 5,186,559 A | * | 2/1993 | Fu | ............... 401/44 |
| 6,003,734 A | * | 12/1999 | Oh | ............ 222/146.6 |
| 6,648,180 B2 | * | 11/2003 | Moon et al. | ............. 222/185.1 |
| 7,150,376 B2 | * | 12/2006 | Tsai | .............. 222/95 |

(Continued)

FOREIGN PATENT DOCUMENTS

JP    12-002447    1/1937

(Continued)

OTHER PUBLICATIONS

International Search Report (PCT/ISA/210) for International Application No. PCT/JP2004/019307, dated Feb. 28, 2005.

(Continued)

*Primary Examiner*—J. Casimer Jacyna
(74) *Attorney, Agent, or Firm*—The Webb Law Firm

(57) ABSTRACT

A liquid storage container (eyedrops container) comprises a container body having a liquid storage portion for containing medical liquid therein, and an instilling portion for allowing the medical liquid to flow out in an opened stage. An aerating device having a filter element and a check valve for allowing ambient air to flow in from outside and preventing the liquid from flowing out to the outside is installed at the bottom of the container body. Further, a cap having an opening member and a valve member is mountable on the container body.

18 Claims, 4 Drawing Sheets

U.S. PATENT DOCUMENTS

| | | |
|---|---|---|
| 2002/0190079 A1 | 12/2002 | Hamamoto |
| 2004/0074925 A1 | 4/2004 | Faurie |
| 2005/0155981 A1 | 7/2005 | Abe et al. |

FOREIGN PATENT DOCUMENTS

| | | |
|---|---|---|
| JP | 39-11991 | 5/1939 |
| JP | 1-110147 | 12/1976 |
| JP | 51-146789 | 12/1976 |
| JP | 6-15636 | 3/1994 |
| JP | 2003063576 | 3/2003 |
| JP | 2003-126218 A | 5/2003 |
| JP | 2004-168423 | 6/2004 |
| WO | WO 02/38464 | 5/2002 |
| WO | WO 04/039305 | 10/2003 |
| WO | WO 03/093132 | 11/2003 |

OTHER PUBLICATIONS

Written Opinion of the International Searching Authority (PCT/ISA/237) for International Application No. PCT/JP2004/013907, dated Aug. 31, 2006.

* cited by examiner

LIQUID STORAGE CONTAINER WITH BOTTOM FILTER

BACKGROUND OF THE INVENTION

1. Field of the Invention

The present invention relates to a liquid storage container comprising a container body including a liquid storage portion for containing liquid therein and an instilling portion for allowing the liquid to flow out of the container in an opened state.

2. Description of the Related Art

An example of the liquid storage container noted above is a medical eyedropper (referred to simply as "eyedropper" hereinafter) for containing medical eyedrops therein for free instillation. As an example of this type of eyedropper, what is called a three-piece type eyedropper is known which includes a main container body in the form of a hollow cylinder having a liquid storage portion for storing the medical liquid therein, an instilling tube attached to the container body, and a cap for sealing the instilling tube to make three components forming a whole eyedropper.

As shown in FIG. 4, what is called a bottle pack eyedropper X is in wide use which includes an integral molding type container A, with an instilling tube 6 and a main container body 10 formed integrally by blow molding or vacuum forming technique, and a cap B screwed or fitted to the container A.

It is also known that the instilling tube has a plug having an instilling opening mounted on a tip end thereof (see Patent Document 1, for example).

As a material of the eyedropper X of this type, a soft thermoplastic resin is used because it is easy to form and so on.

With this type of eyedropper X, when the medical liquid contained in the eyedrops container A shown in FIG. 4 is applied, a barrel 2 of the eyedrops container A (main container body 10) is held by tips of two fingers to keep it in an applying posture where the instilling opening 61a of the eyedrops container A faces an eye to receive the liquid. The barrel 2 is pressed toward an axis of the container while maintaining the applying posture, whereby the medical liquid is instilled and applied from the instilling opening 61a.

In the above-noted eyedroppers, as the medical liquid is instilled and applied from the instilling opening after the eyedropper is opened, the container will tend to return to the original shape before the liquid is discharged, due to the restoring property of the container per se, and thus ambient air flows into the eyedrops container in a volume corresponding to the medical liquid applied. As this type of construction allowing ambient air to flow in, a construction providing an equalizing valve for taking in ambient air is known (Patent Document 2, for example). With this construction, ambient air can be taken in after the medical liquid is instilled and applied to keep the balance between the pressures inside and outside of the container.

The above-noted construction includes a mounting position for an ambient air intake valve provided adjacent the instilling opening. On the other hand, another construction is also known in which the mounting position for the ambient air intake valve is provided so as to face away from the instilling opening (Patent Document 3, for example).

Patent Document 1: U.M. Publication No. 39-11991 (FIGS. 1 to 2)

Patent Document 2: Patent Application "Kokai" No. 51-146789 (see pages 7 to 8, FIG. 4)

Patent Document 3: U.M. Application "Kokai" No. 1-110147 (see Claims, FIG. 2)

The eyedropper disclosed in Patent Document 2 includes a filter member together with the ambient air intake valve, which can prevent the interior of the liquid storage portion from being contaminated by germs when ambient air is drawn in. However, since the mounting position for the ambient air intake valve and the filter member is provided adjacent the instilling opening, it is necessary to provide the instilling opening, the ambient air intake valve and the filter member in the instilling tube, for example, as a result of which the construction around the instilling opening becomes complicated and the sizes of the ambient air intake valve and the filter member are restricted. On the other hand, with the construction disclosed in Patent Document 3 in which the mounting position for the ambient air intake valve is provided to face away from the instilling opening, the construction adjacent the instilling opening is simplified to facilitate manufacture of the container.

Further, with the eyedropper disclosed in Patent Document 2, the instilling opening is directed downward in time of instillation, and thus the liquid contained in the liquid storage portion will constantly contact the ambient air intake valve as long as such a posture is maintained. Although the ambient air intake valve has a construction of a check valve that allows ambient air to flow into the container while prohibiting the liquid from flowing out of the container, it is preferable from a viewpoint of preventing liquid leakage that the ambient air intake valve does not contact the liquid in time of instillation.

In contrast, the construction of the instilling container disclosed in Patent Document 3 includes the ambient air intake valve provided to face away from the instilling opening to prevent the liquid contained in the liquid storage portion from contacting the ambient air intake valve, which eliminates the chance of the liquid leaking from the ambient air intake valve. However, no filter member is provided, and thus there is a risk of contaminating the interior of the liquid storage portion with germs when ambient air is drawn in.

Also, according to the constructions of these eyedroppers and instilling containers, the instilling opening is in a closed state when the container is in storage or otherwise unused for instillation. In this state, when a pressure is applied to the ambient air intake valve due to a shock or the like and ambient air flows into the liquid container portion through the ambient air intake valve, the pressure within the liquid storage portion is increased. If the instilling opening is opened in time of instillation in this state, the increased pressure is released from the instilling opening, which leads to a chance of the liquid of being discharged forcibly from the liquid storage portion.

In such a case, if the eyedropper is designed for controlling a drop amount of liquid in time of instillation to be a predetermined amount, for example, and if the liquid is discharged forcibly in time of instillation as noted above, it is necessary to carry out the instilling operation again to instill and apply the liquid to the eye in order to compensate for the amount of the liquid dispersed to peripheries of the container. This results in problems that the extra instilling operations are required and the liquid is wasted.

The object of the present invention is to provide a liquid storage container capable of preventing liquid from leaking from an ambient air intake valve and of preventing the interior of a liquid storage portion from being contaminated by germs or the like when ambient air is drawn in, as well as capable of preventing a pressure difference from being produced between inside and outside of the container except in time of instillation.

SUMMARY OF THE INVENTION

In order to achieve the above-noted object, a first characteristic feature of a liquid storage container according to the present invention lies in that the container comprises a container body having a liquid storage portion for containing liquid therein, and an instilling portion for allowing the liquid to flow out in an opened state, wherein the container body includes an aerating device provided at the bottom thereof and having a filter element and a check valve for allowing ambient air to flow in from the outside and preventing the liquid from flowing out. Its functions and effects are as follows.

In the case of a container that discharges liquid to the outside by being pressed at the barrel of the container body is pressed to reduce the capacity of the container body, for example, when the pressing operation against the container body is stopped after a desired amount of liquid is discharged to the outside, the container body tends to return to the original shape before the liquid is discharged to the outside by the restoring property of the container body per se. It may be constructed such that, at this time, the interior of the container body is under negative pressure, and ambient air flows into the liquid storage portion from the aerating device in an amount corresponding to the liquid discharged to the outside.

The aerating device having the filter element and check valve is provided at the bottom of the container body and thus faces away from the instilling portion. Therefore, the instilling opening is directed downward in time of instillation. As long as ambient air is drawn in after the instillation while this state is maintained, the liquid contained in the liquid storage portion does not contact the aerating device. There is no chance of the liquid leaking from the aerating device.

The aerating device has the filter element. The filter element is designed not for allowing entry of a source of contamination such as germs present in ambient air. Ambient air drawn from the aerating device passes through the filter element, which can prevent contamination in the interior of the liquid storage portion.

Further, the aerating device has the check valve for allowing air to flow in from the outside while prohibiting the liquid from flowing out. Thus, it is possible to balance pressure between inside and outside of the container by drawing ambient air at the check valve. The check valve can prevent the liquid from leaking from the aerating device in time of storage or the like in order to check any discharge of the liquid.

If the aerating device is provided adjacent the instilling opening as in the eyedropper disclosed in Patent Document 2, it is necessary to take the positional relationship between the aerating device and the instilling opening into consideration, and thus the aerating device is restricted in design such as in size or the like. However, the construction providing the aerating device having the filter element and check valve at the bottom of the container body will less restrict the designs of the filter element and the check valve in their sizes or the like as long as they are contained within the range of the size of the bottom of the container body. In other words, the degree of freedom in designing the aerating device is increased to facilitate manufacture of the liquid storage container.

As described above, since the liquid storage container includes the aerating device provided at the bottom of the container body, the center of gravity of the liquid storage container is shifted toward the bottom of the container body by a degree corresponding to the weight of the aerating device. As a result, stability is improved when the liquid storage container is placed on a floor surface with the bottom of the container body contacting the floor surface, compared with the construction having the aerating device provided adjacent the instilling opening. Therefore, the liquid storage container does not easily fall down, which constitute a construction suitable for storage.

A second characteristic feature of the liquid storage container according to the present invention lies in that the aerating device has a receiving portion contacting a floor surface and supporting the container body. Its function and effect are as follows.

As the aerating device has a receiving portion contacting a floor surface and supporting the container body, it is possible to allow the floor surface to contact the liquid storage container in a constant condition when the liquid storage container is placed on the floor surface with the receiving portion contacting the floor surface. As a result, the liquid storage container can be placed on the floor surface in a balanced manner.

A third characteristic feature of the liquid storage container according to the present invention lies in that a bottom cap is provided for covering the aerating device. Its functions and effects are as follows.

When the bottom cap is mounted for covering the aerating device as above, the construction can prevent external pressure variations from directly affecting the aerating device. As a result, even when a certain pressure is applied to the aerating device, ambient air has little chance of flowing into the liquid storage portion from the aerating device, which can effectively prevent a pressure increase within the liquid storage portion caused by the pressure variations.

Therefore, it is possible to prevent a difference in pressure from being produced between inside and outside of the container when the bottom cap is attached. This provides a construction capable of preventing a pressure increased at a time other than a time of instillation from being released from the instilling portion in time of instillation and thereby allowing the medical liquid contained in the liquid storage portion to be ejected forcibly. Thus, any re-instilling operation is not required and the liquid is not wasted in time of instillation. Further, the aerating device can be well protected when the bottom cap is attached.

A fourth characteristic feature of the liquid storage container according to the present invention lies in that the bottom cap is formed integrally with the container body to be separable from the container body. Its functions and effects are as follows.

With this construction, the bottom cap can be made of parison which is the same material as the container body in forming the liquid storage container by blow molding or vacuum forming technique, for example.

Therefore, the liquid storage container provided with the bottom cap may be readily manufactured.

Also, since the bottom cap is separable from the container body, the aerating device is exposed when the bottom cap is cut off and removed. The bottom cap can easily be cut off along a cut-off line such as perforations and prevented from being removed in any distorted shape. This can improve convenience in use.

On the other hand, the aerating device has little chance of being exposed unless the user intentionally cuts off and removes the bottom cap, which can substantially eliminate a possibility that the bottom cap is inadvertently removed during transportation. Thus, the aerating device can be well protected until use of the liquid storage container.

A fifth characteristic feature of the liquid storage container according to the present invention lies in that the check valve has a duck-bill type construction including a pair of plate-shaped portions contactable with each other at end portions thereof, and is closed when the pair of plate-shaped portions contact each other at the end portions thereof or opened when the pair of plate-shaped portions are moved away from each other at the end portions thereof. Its functions and effects are as follows.

Explanation will be given hereinafter taking for example the container in which the container body is pressed to discharge the liquid from the liquid storage container.

When the check valve has the construction of the duck-bill type noted above, the check valve has the pair of plate-shaped portions contacting each other at the end portions thereof. Thus, each of the plate-shaped portions has a tapered face.

Thus, in a normal state when the instilling operation is not carried out, the check valve is closed with the pair of plate-shaped portions contacting each other at the end portions thereof (closed state).

The interior of the container body is under positive pressure while the container body is pressed. At this time, as ambient air does not flow into the liquid storage portion, no pressure of incoming ambient air acts on the tapered faces (FIG. 1: 104a, b), and thus the contact between the end portions of the tapered faces is not canceled (closed state: FIG. 1). Therefore, the medical liquid does not flow out of the aerating device, nor does ambient air flow in while the container body is pressed to discharge the medical liquid.

On the other hand, when the pressing operation is stopped, the container body tends to return to the original shape before the medical liquid is discharged to the outside, due to the restoring property of the container per se. At this time, the interior of the container body comes under negative pressure. Then, the pressure of the entering ambient air acts on an inner side of each of the tapered faces, and the contact between the end portions thereof is canceled (FIG. 2). As a result, the aerating device is brought to an open state. Thus, ambient air flows into the liquid storage portion in a volume corresponding to the medical liquid discharged.

Hence, according to the liquid storage container of the fifth characteristic feature of the present invention, the duck-bill construction of the check valve can bring the check valve to the closed state when the container body is pressed to discharge the liquid (the interior of the container body comes under positive pressure).

Further, when the pressing operation against the container body is stopped after the medical liquid is discharged and the container body tends to return to the original shape before the medical liquid is discharged (the interior of the container body comes under negative pressure), the check valve is placed in the opened state by making effective use of the pressure of the entering ambient air.

Therefore, it is possible to provide the check valve for timely allowing ambient air to flow in from the outside and not allowing the medical liquid to be discharged to the outside depending on whether or not the liquid is discharged.

A sixth characteristic feature of the liquid storage container according to the present invention lies in that the container further comprises a cap attachable to the container body and including an opening member for opening the instilling portion in an unopened state and a valve member for allowing the liquid to flow out and preventing ambient air from flowing into the container.

When the cap is attached to the container body containing the liquid therein in an unopened state, the sealed condition can be cancelled by the opening member. On the other hand, the sealed condition of the container body can be maintained reliably until the instilling portion is opened by the opening member.

Further, this cap includes the valve member for allowing the liquid to be discharged to the outside and preventing the ambient air from flowing in from the outside, which can block passages through which ambient air flows into the container body after a desired amount of liquid is discharged to the outside. Thus, it is possible to prevent germs present in ambient air from being taken into the eyedrops container after the container is opened, and eventually prevent contamination within the container after the container is opened.

DETAILED DESCRIPTION OF THE INVENTION

An embodiment of the present invention will be described hereinafter with reference to the accompanying drawings.

Figure 1:
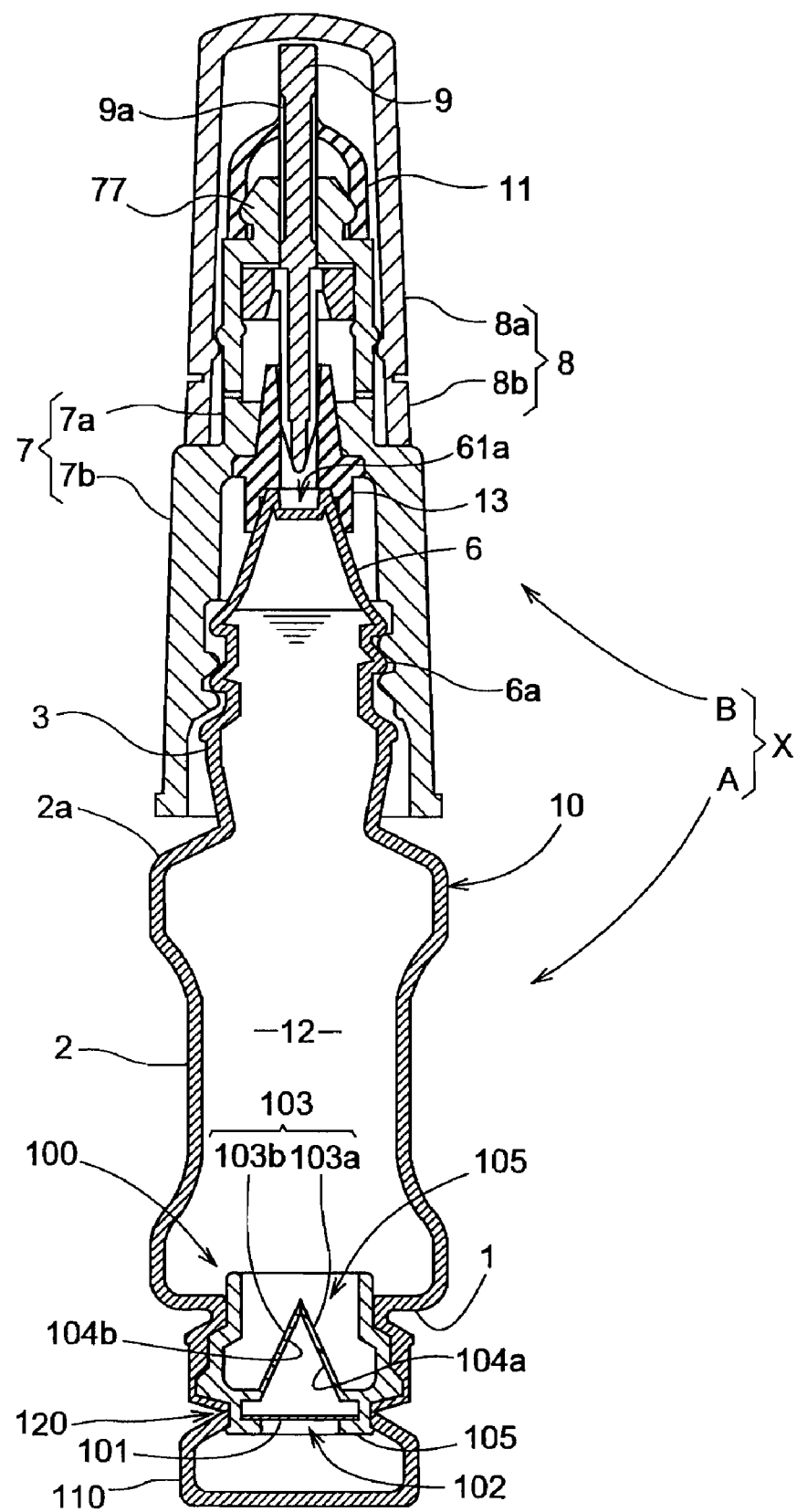
FIG. 1 is a schematic view of a liquid storage container (eyedropper) according to the present invention.

FIG. 1 shows a schematic view of an eyedropper X used mainly for medical purposes. The eyedropper X comprises an eyedrops container A including a container body 10 for containing medical liquid such as medical eyedrops or the like as liquid, and a cap B detachably mounted on the eyedrops container A.

The illustrated eyedrops container A includes the container body 10 having a liquid storage portion 12 in the form of a hollow cylinder for containing the medical liquid, and an instilling tube 6 formed on the container body 10 with an instilling portion (instilling opening) 61a formed at a tip end thereof. The eyedrops container A may have the container body 10 and the instilling tube 6 integrally formed by blow molding or vacuum forming technique.

The eyedrops container A includes a circular bottom 1, a barrel 2 in the form of a hollow cylinder continuous with a periphery of the bottom, a cylindrical neck portion 3 formed continuous from a shoulder portion 2a of the barrel 2, and the instilling tube 6 continuous upward from the neck portion 3. The instilling tube 6 includes a male screw 6a formed on outer peripheries thereof.

A plug may be provided in the tip end of the instilling tube 6 (not shown). The plug is in wide use because the manufacturing cost is reduced compared with the case where the instilling opening 61a is formed directly in the instilling tube 6 by using the blow molding or vacuum forming technique. In this case, the plug is attached in tight contact with the instilling tube 6 to prevent ambient air from flowing in.

The eyedrops container A may be made of a thermoplastic material such as polyethylene, polyethylene-polypropylene, polypropylene, polyethylene-terephthalate, polycarbonate or the like. The eyedrops container A formed is elastically deformable as a whole.

The cap B may employ any construction as long as it is detachably screwed to the male screw 6a of the eyedrops container A (the details will be described later). In this case, it is preferable to achieve the effect of reliably maintaining a sealed condition of the eyedropper X until use, preventing leakage of the medical liquid contained in the liquid storage portion 12 after the eyedropper X is opened, or preventing contamination of the interior of the liquid storage portion 12 efficiently by preventing germs present in ambient air from being taken into the eyedrops container A.

In the present invention, the eyedrops container A includes an aerating device 100 provided at the bottom of the container body 10. The aerating device 100 has a filter element 101, and a check valve 103 for allowing ambient air to flow in while preventing the medical liquid from being discharged to the outside. The aerating device 100 is attached to an opening 102 formed in the bottom of the container body 100.

This aerating device 100 allows ambient air to flow in at the check valve 103 and makes it possible to balance the pressure within the container with the outside.

More particularly, in executing an instilling operation, the barrel 2 of the eyedrops container A (container body 10) is held by two fingers to press the barrel 2 toward an axis of the container to reduce the capacity of the container body 10 thereby to discharge the medical liquid. When the pressing operation is stopped after a desired amount of liquid is discharged, the container will tend to return to the original shape before the liquid is discharged, due to the restoring property of the container body 10 per se. In this case, the interior of the container body 10 is under negative pressure, and thus ambient air may flow into the liquid storage portion 12 from the aerating device 100 in a volume corresponding to the liquid discharged.

It is possible to provide the filter element 101 of the check valve 103 outwardly, for example, so as not to allow entry of a source of contamination such as germs present in ambient air. With this construction, since ambient air drawn from the aerating device 100 passes through the filter element 101 first, it is possible to prevent the medical liquid within the container body 10 from being contaminated even after the sealed condition of the eyedrops container A is cancelled. Also, with the construction in which the check valve 103 allows ambient air to enter from the outside while preventing the liquid from being discharged, it is possible to balance the pressure between the container body 10 and the outside by allowing ambient air to flow in at the check valve 103.

The aerating device 100 preferably includes a receiving portion 105 for contacting a floor surface and supporting the container body 10. With this construction, the eyedrops container A can be placed on the floor surface in a balanced manner.

As noted above, the eyedrops container A is elastically deformable. Even if the shape of the bottom of the container body 10 remains deformed and distorted, the eyedrops container A can be steadily placed on the floor surface as the aerating device 100 has the receiving portion 105.

Further, a bottom cap 110 is provided for covering the aerating device 100. This construction, with the bottom cap 110 attached, can prevent external pressure variations from directly affecting the aerating device 100. As a result, even when a certain pressure is applied to the aerating device 100, ambient air has no chance of flowing into the liquid storage portion 12 from the aerating device 100, which can effectively prevent a pressure increase within the liquid storage portion 12 due to the pressure variations.

Further, the aerating device 100 can be well protected when the bottom cap 110 is attached.

Therefore, it is possible to prevent the pressure increased at a time other than a time of instillation from being released from the instilling opening 61a in time of instillation, and prevent the medical liquid contained in the liquid storage portion 12 from being ejected forcibly. Thus, any repetition of instilling operation is not required and the liquid is not wasted.

More particularly, the provision of the bottom cap 110 for covering the aerating device 100 can prevent a pressure difference from being produced between the inside and outside of the container body 10.

The bottom cap 110 preferably is formed integrally with the container body 10 and is separable by cutting from the container body 10. A boundary between the container body 10 and the bottom cap 110 may have a separating portion 120 in the form of perforations, for example.

With this construction, the bottom cap 110 can be made of parison which is the same material as the container body 10 in forming the container body 10 by the blow molding or vacuum forming technique, for example, as described later.

Therefore, the container body 10 provided with the bottom cap 110 may be readily manufactured.

Also, since the bottom cap 110 is separable from the container body 10, the aerating device 100 is exposed when the bottom cap 110 is cut off after the eyedropper X is opened. The bottom cap 110 can be easily cut off along the separable portion 120 such as perforations to be prevented from being removed in any distorted shape. This can improve convenience in use.

On the other hand, the aerating device 100 has little chance of being exposed unless the user intentionally cuts off and removes the bottom cap 110, which can substantially eliminate a possibility that the bottom cap 110 is inadvertently removed during transportation of the eyedropper X. Thus, the aerating device 100 can be well protected until use of the eyedropper X.

The check valve 103 preferably comprises a duck-bill type construction including a pair of plate-shaped portions 103a and 103b contactable with each other at end portions thereof, which is closed when the end portions of the pair of plate-shaped portions 103a and 103b contact each other or opened when the end portions of the pair of plate-shaped portions 103a and 103b move away from each other.

The pair of plate-shaped portions 103a and 103b have a tapered construction in which the pair of plate-shaped portions 103a and 103b contact each other at the end portions thereof. Thus, the plate-shaped portions 103a and 103b have tapered faces 104a and 104b, respectively.

In a normal state when an instilling operation is not executed, the check valve is closed with the pair of plate-shaped portions 103a and 103b contacting each other at the end portions thereof (closed state).

On the other hand, in executing an instilling operation, the barrel 2 of the eyedrops container A (container body 10) is held by two fingers to press the barrel 2 toward the axis of the container. With this pressing operation, the interior of the eyedrops container A comes under positive pressure and thus the medical liquid is forced out of the instilling opening 61a to be instilled and applied.

When the instilling operation is stopped after the medical liquid is instilled and applied, the eyedrops container A will tend to return to the original shape before the medical liquid is applied, due to the restoring property of the container per se. At this time, the interior of the eyedrops container A comes under negative pressure and ambient air flows into the liquid storage portion 12 in a volume corresponding to the medical liquid applied.

The interior of the eyedrops container A (container body 10) is under positive pressure while the barrel 2 of the eyedrops container A (container body 10) is pressed. At this time, as ambient air does not flow into the liquid storage portion 12, the pressure from ambient air does not act on the tapered faces 104a and 104b (on the side of the filter element 101) of the plate-shaped portions 103a and 103b, and thus the contact between the end portions of the plate-shaped portions 103a and 103b is not canceled (i.e. the check valve remains in the closed state; see FIG. 1). Therefore, the medical liquid does not flow out of the aerating device 100 and ambient air does not flow in while the user presses the barrel 2 of the eyedrops container A to instill and apply the medical liquid.

On the other hand, when the pressing operation is stopped, ambient air is forced to flow into the liquid storage portion 12 in a volume corresponding to the medical liquid applied. At this time, as ambient air flowing in through the filter element 101 passes through the opening 102, the pressure of the entering ambient air acts on each of the tapered faces 104a and 104b. Then, the contact between the end portions of the plate-shaped portions 103a and 103b is canceled. As a result, the aerating device 100 is brought to an open state (see FIG. 2) in which ambient air flows into the liquid storage portion 12 through an ambient air intake bore 105.

Thus, the check valve 103 of the duck-bill type noted above allows the aerating device 100 to be in the closed state when the barrel 2 of the eyedrops container A is pressed in applying the medical liquid (the interior of the eyedrops container A comes under positive pressure).

Further, when the pressing operation against the barrel 2 of the eyedrops container A is stopped after the medical liquid is applied and the eyedrops container A tends to return to the original shape before the medical liquid is instilled and applied (the interior of the eyedrops container A comes under negative pressure), the aerating device 100 is placed in the opened state by making effective use of the pressure of the entering ambient air.

Therefore, it is possible to provide the check valve 103 for allowing ambient air to flow into the container and prohibiting the medical liquid from being discharged, in a manner timed with the instilling operation.

The construction of the eyedrops container A has been described so far. The cap B to be attached to the eyedrops container A will be described hereinafter.

As noted above, the cap B detachably screwed to the male screw 6a of the eyedrops container A is usable in the present invention.

For instance, the cap B may have a construction including an opening member for opening the instilling portion 61a in an unopened state, and a valve member for allowing the liquid to be discharged to the outside and preventing ambient air from flowing in.

More particularly, as shown in FIG. 1, the cap B includes a base member 7 attachable to the eyedrops container A for storing the medical liquid therein, and an over cap 8 attachable to the base member 7. The over cap 8 includes a push-in member (opening member) 9 having grooves 9a formed in a side face thereof for guiding the medical liquid to the outside, the push-in member being inserted into and supported by the base member 7 to be sidable relative thereto and pushable toward the eyedrops container A by the over cap 8 to break the sealed condition of the eyedrops container A, a first tight contact member (valve member) 11 provided in a tip end portion 77 of the base member 7 in tight contact with the push-in member 9 from the outside, and a second tight contact member 13 provided on inner peripheries of the base member 7 to be contactable with the push-in member 9 pushed in.

One example of the preferable embodiments of the over cap 8 may include a cap body 8a and a separable part 8b to be cut and removed from the cap body 8a. When the separable part 8b is removed and the cap body 8a is pushed in (see FIG. 2), the cap body 8a pushes the push-in member 9 toward the eyedrops container A to allow the cap body 8a to contact the base member 7.

Also, the base member 7 may include a first base element 7a and a second base element 7b.

Figure 2:
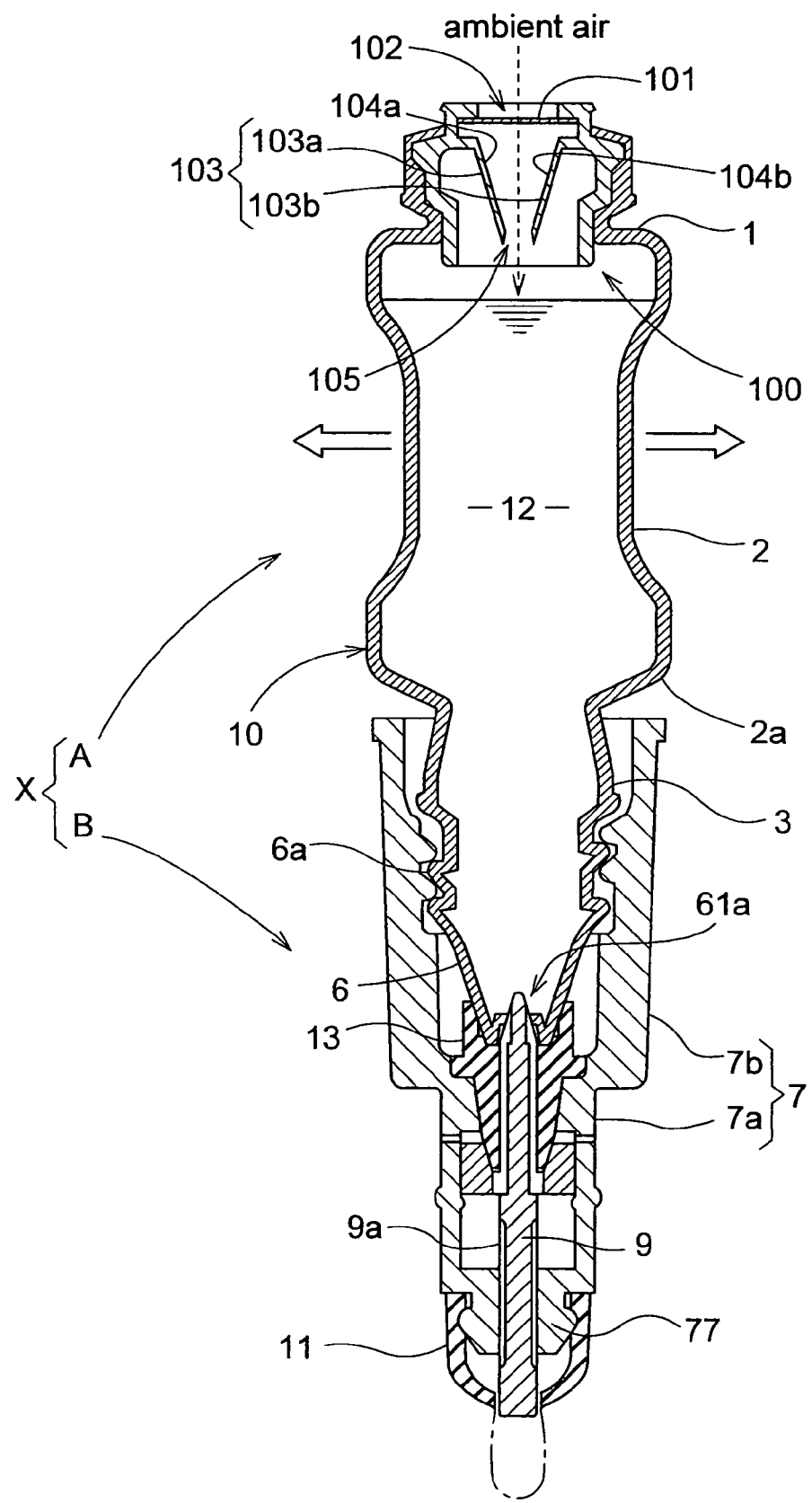
FIG. 2 is a schematic view of an aerating member in an opened stage.

When the eyedropper A is not used yet, the eyedrops container A maintains the sealed condition (FIG. 1). Since any push-in operation is not executed against the push-in member 9 (opening member) of the cap B, the medical liquid before opening the container is prevented from contacting ambient air, which can reliably maintain the sealed condition of the unused eyedrops container A. Then, the push-in member 9 is fitted into the eyedrops container A (to open the instilling portion 61a in the unopened condition) by pushing in the push-in member 9, thereby to reliably break the sealed condition of the eyedrops container A (FIG. 2).

The liquid flowing out of the eyedrops container A after breaking the sealed condition is guided to the outside through the grooves 9a formed in the side face of the push-in member 9. At this time, since the second tight contact member 13 provided on the inner peripheries of the base member 7 contacts the push-in member 9 tight, the medical liquid can be prevented from flowing out through passages other than the grooves 9a. Thus, it is possible to restrain the liquid from leaking from the container body 10 in use.

Further, since the first tight contact member 11 (valve member) provided in the tip end portion 77 of the base member 7 to contact the push-in member 9 tight from the outside is easily moved away from the push-in member 9 by pressure of the medical liquid guided by the grooves 9a, the medical liquid is allowed to flow out, which facilitates application of the medical liquid.

The first tight contact member 11 is positioned in tight contact the push-in member 9 from the outside again after a desired amount of the medical liquid is discharged to the outside, which can block passages through which ambient air flows into the container body 10. Thus, it is possible to prevent germs present in ambient air from being taken into the eyedrops container A after the eyedrops container A is opened, and eventually prevent contamination within the container after the eyedrops container A is opened.

The cap B may be made of a thermoplastic material such as polyethylene, polyethylene-polypropylene, polypropylene, polyethylene-terephthalate, polycarbonate or the like.

A method of manufacturing the eyedrops container A in the eyedropper X according to the present invention will be described hereinafter.

The eyedrops container A is formed by the blow molding or vacuum forming technique, for example.

Figure 3:
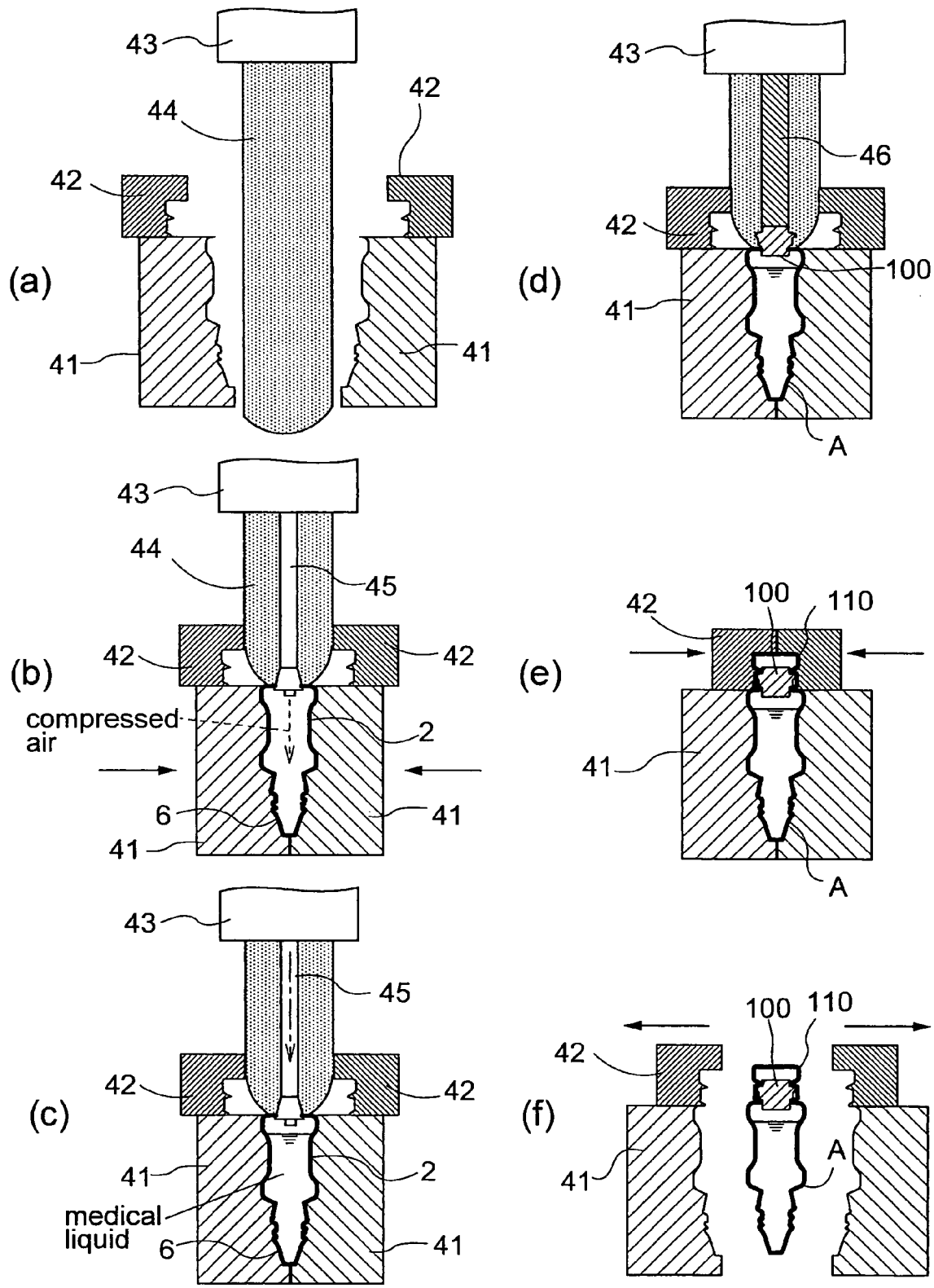
FIG. 3 is a schematic view of a method of manufacturing an eyedrops container A.
Figure 4:
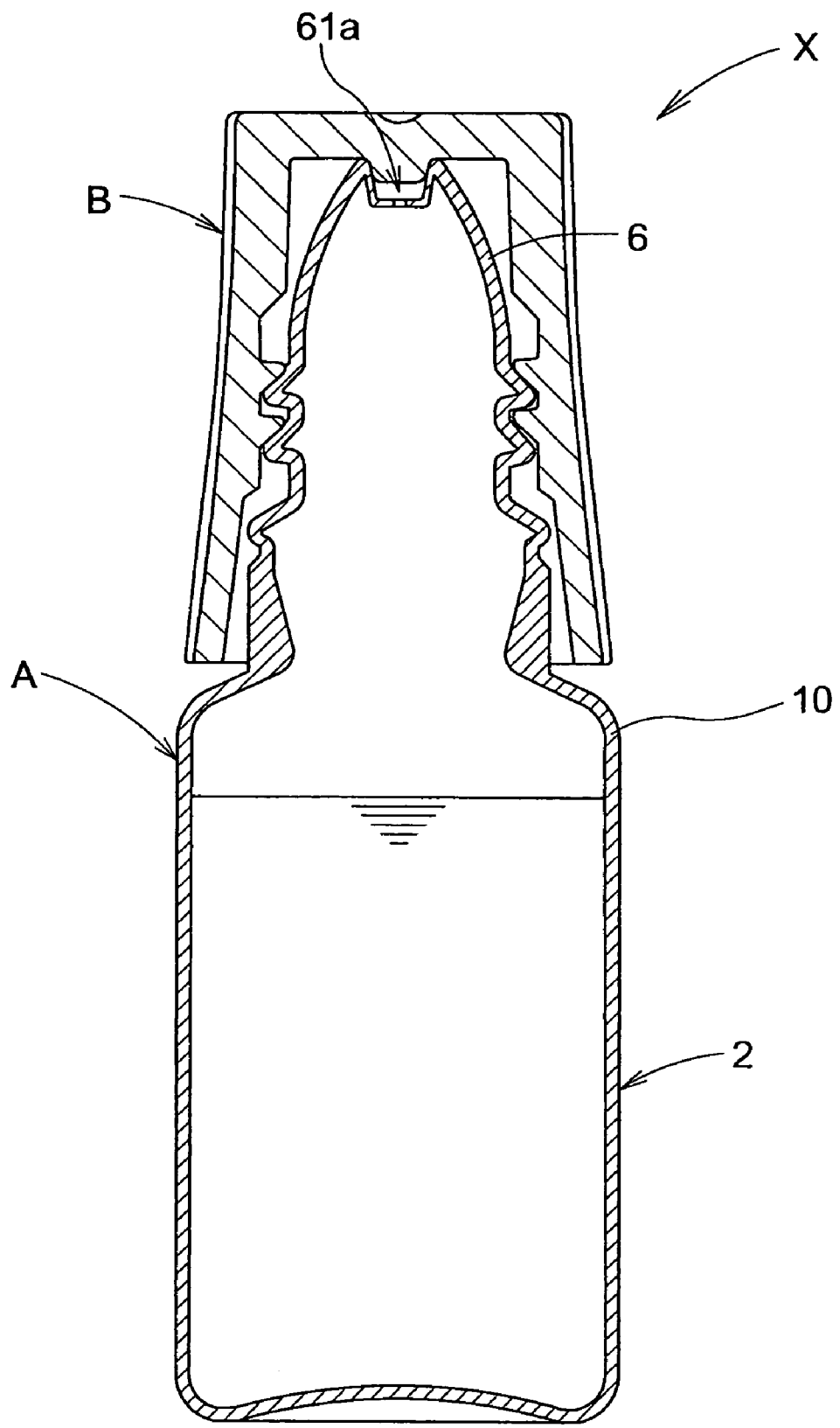
FIG. 4 is a schematic view of a conventional eyedrops container.

In the present embodiment, an example is shown in which the bottom cap 110 is formed integrally with the eyedrops container A (container body 10) by blow-fill sealing technique which is an integrated system comprising the steps of blow-molding the container, filling the container with the medical liquid and closing the container (see FIG. 3).

(a) A pair of main molds 41 for molding the barrel 2 and the instilling tube 6 and a pair of auxiliary molds 42 for molding the bottom cap 110 and for caulking the container body 10 with the aerating device 100 to be formed integrally with each other are arranged in open positions, respectively. A hollow cylindrical parison 44 is extruded from an extruding head 43 arranged above the molds to be placed between both of the molds 41 and 42.

(b) The main molds 41 are closed and compressed air is blown from a nozzle 45 to expand the parison 44 thereby to mold the barrel 2 and the instilling tube 6.

(c) A predetermined quantity of medical liquid is filled by the nozzle 45.

(d) The aerating device 100 manufactured in a separate process is placed in a predetermined position (the bottom position of the eyedrops container A) by a setting nozzle 46.

(e) The auxiliary molds 42 are closed after the setting nozzle 46 is raised, to caulk the container body 10 with the aerating device 100, and to mold the bottom cap 110.

(f) The main molds 41 and the auxiliary molds 42 are opened and the eyedrops container A is taken out of the molds.

The boundary between the container body 10 and the bottom cap 110 preferably has a small thickness, for example, so that the bottom cap 110 may easily be cut and removed.

Thus, the bottom cap 110 may be made of parison 44 that is the same material as the container body 10, as a result of which the container body 10 provided with the bottom cap 110 can be readily manufactured.

The present invention is applicable to a liquid storage container including a container body having a liquid storage portion for containing liquid therein and an instilling portion for allowing the liquid to flow out in an opened state. Such a liquid storage container can be used as a medical eyedropper for containing medical eyedrops therein for instillation.

The invention claimed is:

1. An eye drop container comprising:
   a container body having a liquid storage portion for containing liquid therein;
   an instilling portion provided at the top of the container for allowing the liquid to flow out in an opened stage;
   an aerating device provided at the bottom of the container body and having a filter element and a check valve for allowing ambient air to flow in from the outside and preventing the liquid from flowing out; and
   an attachable bottom cap for covering the aerating device, the aerating device being allowed to contact a floor surface when the bottom cap is removed to steadily support the container on the floor surface in a balanced manner.

2. The eye drop container as defined in claim 1, including an opening member for opening the instilling portion in an unopened stage and a valve member for allowing the liquid to flow out and preventing ambient air from flowing into the container.

3. The eye drop container as defined in claim 1, wherein the filter element is designed not for allowing entry of a source of contamination present in the ambient air.

4. The eye drop container as defined in claim 1, wherein the aerating device is designed for allowing entry of the ambient air into the liquid storage portion from the outside.

5. The eye drop container as defined in claim 1, wherein the liquid is allowed to flow out in association with reduction in volume of the container body under the opened stage.

6. The eye drop container as defined in claim 1, wherein the filter element is designed not for allowing entry of a source of contamination present in the ambient air into the container, and the aerating device is designed for allowing entry of the ambient air into the liquid storage portion from the outside.

7. The eye drop container as defined in claim 6, wherein the liquid is allowed to flow out in association with reduction in volume of the container body under the opened stage.

8. The eye drop container as defined in claim 1, wherein the bottom cap is formed integrally with the container body.

9. The eye drop container as defined in claim 8, wherein the bottom cap formed integrally with the container body is separable from the container body.

10. The eye drop container as defined in claim 9, wherein the aerating device comprises a receiving portion to contact the floor surface to steadily support the container.

11. The eye drop container as defined in claim 10, wherein the check valve has a duck-bill type construction including a pair of plate-shaped portions contactable with each other at end portions thereof, and is closed when the pair of plate-shaped portions contact each other at the end portions thereof or opened when the pair of plate-shaped portions are moved away from each other at the end portions thereof.

12. The eye drop container as defined in claim 10, including an opening member for opening the instilling portion in an unopened stage and a valve member for allowing the liquid to flow out and preventing ambient air from flowing into the container.

13. The eye drop container as defined in claim 10, wherein the filter element is designed not for allowing entry of a source of contamination present in the ambient air.

14. The eye drop container as defined in claim 10, wherein the aerating device is designed for allowing entry of the ambient air into the liquid storage portion from the outside.

15. The eye drop container as defined in claim 9, wherein the check valve has a duck-bill type construction including a pair of plate-shaped portions contactable with each other at end portions thereof, and is closed when the pair of plate-shaped portions contact each other at the end portions thereof or opened when the pair of plate-shaped portions are moved away from each other at the end portions thereof.

16. The eye drop container as defined in claim 1, wherein the aerating device is opposite to the instilling portion and further comprises an outer supporting surface to contact the floor surface when the bottom cap is removed, wherein the filter and the check valve are spaced from the outer supporting surface and between the instilling portion and the outer supporting surface of the aerating device.

17. An eye drop container comprising:
   a container body having a liquid storage portion for containing liquid therein;
   an instilling portion for allowing the liquid to flow out in an opened stage, the instilling portion comprising an opening member for opening the instilling portion in an unopened stage and a valve member for allowing the liquid to flow out and preventing ambient air from flowing into the container, wherein the valve member prevents the ambient air from flowing into the container when the valve member is in tight contact with the opening member from its outside and allows the liquid to flow out when the valve member is away from the opening member due to pressure of the liquid;
   an aerating device provided at the bottom of the container body and having a filter element and a check valve for allowing ambient air to flow in from the outside and preventing the liquid from flowing out; and
   an attachable bottom cap for covering the aerating device, the aerating device being allowed to contact a floor surface when the bottom cap is removed.

18. An eye drop container comprising:
   a container body having a liquid storage portion for containing liquid therein;
   an instilling portion for allowing the liquid to flow out in an opened stage, the instilling portion comprising an opening member for opening the instilling portion in an unopened stage and a valve member for allowing the liquid to flow out and preventing ambient air from flowing into the container, wherein the valve member prevents the ambient air from flowing into the container when the valve member is in tight contact with the opening member from its outside and allows the liquid to flow out when the valve member is away from the opening member due to pressure of the liquid;

an aerating device provided at the bottom of the container body and having a filter element and a check valve for allowing ambient air to flow in from the outside and preventing the liquid from flowing out, wherein the aerating device comprises a receiving portion to contact the floor surface to steadily support the container; and an attachable bottom cap for covering the aerating device, the aerating device being allowed to contact a floor surface when the bottom cap is removed, wherein the bottom cap is formed integrally with the container body and is separable from the container body.

* * * * *